United States Patent
Martell et al.

[11] Patent Number: 5,987,965
[45] Date of Patent: Nov. 23, 1999

[54] GAS SENSOR WITH CONDUCTIVE HOUSING PORTIONS

[75] Inventors: Dennis Martell, Naperville, Ill.; Richard Grove Warburton, Coraopolis, Pa.; Laura Ann Lindner, Oakdale, Pa.; Juergen Lindner, Bethel Park, Pa.

[73] Assignees: J and N Associates, Inc., Valparaiso, Ind.; National Draeger Incorporated, Pittsburgh, Pa.

[21] Appl. No.: 09/172,487

[22] Filed: Oct. 14, 1998

Related U.S. Application Data

[60] Continuation of application No. 08/889,648, Jul. 8, 1997, Pat. No. 5,827,948, which is a division of application No. 08/515,688, Aug. 16, 1995, Pat. No. 5,744,697.

[51] Int. Cl.$^6$ .................................................. G01N 21/77
[52] U.S. Cl. ...................... 73/31.06; 73/31.05; 73/23.31; 204/412; 204/431
[58] Field of Search ............................... 73/31.06, 23.31, 73/31.05; 204/412, 415, 431

[56] References Cited

U.S. PATENT DOCUMENTS

| | | |
|---|---|---|
| 3,622,488 | 11/1971 | Chand et al. . |
| 3,776,832 | 12/1973 | Oswin et al. . |
| 3,878,080 | 4/1975 | Luck . |
| 3,909,386 | 9/1975 | Oswin et al. . |
| 4,036,724 | 7/1977 | Binder et al. . |
| 4,171,253 | 10/1979 | Nolan et al. . |
| 4,329,214 | 5/1982 | Spritzer et al. . |
| 4,478,704 | 10/1984 | Miyoshi et al. . |
| 4,525,266 | 6/1985 | Schmidt et al. ........................ 204/412 |
| 4,621,035 | 11/1986 | Bruder . |
| 4,688,021 | 8/1987 | Buck et al. . |
| 4,695,361 | 9/1987 | Grady . |
| 4,717,633 | 1/1988 | Hauser . |
| 4,767,994 | 8/1988 | Hopkins et al. . |
| 4,816,355 | 3/1989 | Kulibert et al. . |
| 4,874,500 | 10/1989 | Madou et al. .......................... 204/412 |
| 4,900,643 | 2/1990 | Eskra et al. . |
| 4,948,681 | 8/1990 | Zagrodnik et al. . |
| 5,126,035 | 6/1992 | Kiesele et al. . |
| 5,173,166 | 12/1992 | Tomantschger et al. . |
| 5,183,549 | 2/1993 | Joseph et al. ...................... 204/412 X |
| 5,183,550 | 2/1993 | Mattiessen .......................... 204/412 X |
| 5,250,171 | 10/1993 | Warburton et al. ..................... 204/431 |
| 5,281,324 | 1/1994 | Kiesele et al. ...................... 204/412 X |
| 5,302,274 | 4/1994 | Tomantschger et al. ............... 204/412 |
| 5,314,605 | 5/1994 | Matthiessen ........................ 204/412 X |
| 5,331,310 | 7/1994 | Stetter et al. ........................... 340/632 |
| 5,336,390 | 8/1994 | Busack et al. ......................... 204/431 |
| 5,573,648 | 11/1996 | Shen et al. ............................. 204/412 |

FOREIGN PATENT DOCUMENTS

| | | |
|---|---|---|
| 0298570 | 1/1989 | European Pat. Off. . |
| 0762116 | 3/1997 | European Pat. Off. . |
| 4025635 | 2/1991 | Germany . |

OTHER PUBLICATIONS

Japanese Patent Abstract No. 62218852, dated Sep. 26, 1987.
Japanese Patent Abstract No. 4134234, dated May 8, 1992.
Blurton et al., "Controlled–Potential Electrochemical Analysis of Carbon Monoxide," American Laboratory, Jul. 1974, 5 pages.
Bay et al., "Electrochemical Technique for the Measurement of Carbon Monoxide," Analytical Chemistry, vol. 46, Oct. 1974, pp. 1837–1839.

*Primary Examiner*—Daniel S. Larkin
*Attorney, Agent, or Firm*—Marshall, O'Toole, Gerstein, Murray & Borun

[57] ABSTRACT

A gas sensor assembly having a first housing portion having a receptacle formed therein and a second housing portion in the form of a cover. A gas-sensing agent is disposed in the receptacle, and a working electrode, a counter electrode, and a reference electrode provided on a single electrode support sheet are disposed in fluid contact with the gas-sensing agent. The first housing portion is provided with three conductive housing portions which are in electrical contact with the three electrodes, and the cover maintains pressurized contact between the three conductive housing portions and the three corresponding electrodes. The gas sensor may be provided with two different types of leakage detectors to sense leakage of the gas-sensing agent from the sensor.

20 Claims, 2 Drawing Sheets

GAS SENSOR WITH CONDUCTIVE HOUSING PORTIONS

This is a continuation of allowed U.S. Ser. No. 08/889,648 filed Jul. 8, 1997, now U.S. Pat. No. 5,827,948 which is a divisional of U.S. Ser. No. 08/515,688 filed Aug. 16, 1995, now U.S. Pat. No. 5,744,697.

BACKGROUND OF THE INVENTION

The present invention is directed to a gas sensor used to detect the presence of gases, such as carbon monoxide.

Most commercially available gas sensors are of the amperometric type having two or more electrodes in which a catalytically active metal is fixed to a porous substrate. The porous substrate operates as a gas permeable membrane. The electrodes are located on the inside surface of the membrane where they are immersed in an electrolyte such as sulfuric acid. External circuitry maintains one of the electrodes, the working electrode, at a given electrical potential with respect to one of the other electrodes.

When the gas of interest diffuses through the porous membrane to reach the working electrode, the diffused gas is oxidized or reduced at the interface of the working electrode and the electrolyte. That reaction generates an electrical current that is proportional to the concentration of the gas. In some cases, the gas of interest reacts with another chemical which, in turn, is oxidized or reduced. In some cases, sensors are of a galvanic design wherein a metal such as lead is oxidized to provide the potential at the working electrode.

In the prior art, the sensors were connected to the external circuit through wires. For example, a platinum contact wire was connected to the catalytically active electrode and passed through the sensor body to an external contact. Since most sensors contain a corrosive, liquid electrolyte, a difficulty with sensors has been provides secure electrical contact with the electrodes while maintaining a seal at the location where the conductor passes through the sensor body. In the prior art, seals around conductors have included gaskets made of TEFLON brand material. In other methods, the seal has been made of thermoplastic material or epoxy resin.

One difficulty with such prior art sensors has been that such seals were difficult and expensive to make. Accordingly, there was a need in the prior art for an improved sensor design that would avoid the need for such seals and thereby be more reliable and less expensive to manufacture. Also, there was a need for a sensor that was mechanically stronger and more durable than sensors known in the prior art wherein the electrodes were connected to platinum wires.

Previous carbon monoxide sensors are relatively complicated in design and suffer from a number of disadvantages due to the use of sulfuric acid, which is typically used as the electrolyte. These disadvantages include the fact that the sulfuric acid may leak from the sensor and/or cause the internal components of the sensor to corrode.

SUMMARY OF THE INVENTION

The present invention is directed to a gas sensor assembly having a housing with a receptacle formed therein, a gas-sensing agent disposed in the receptacle, and a plurality of electrodes disposed in fluid contact with the gas-sensing agent. The housing has a non-conductive housing portion and a plurality of conductive housing portions, each of the conductive housing portions being conductively separated from each other by the non-conductive housing portion. Each of the conductive housing portions is conductively separated from the electrodes, and each of the conductive housing portions is composed of a conductive plastic material.

The housing may have a contact surface that is formed by a portion of the non-conductive housing portion and a portion of each of the conductive housing portions, the gas sensor assembly may also include an electrode plate disposed adjacent the contact surface of the housing, and the electrodes may be disposed on the electrode plate. The housing may have a surface that is formed by a portion of the non-conductive housing portion and a portion of each of the conductive housing portions.

The housing may have a first surface and a second surface, a first portion of each of the conductive housing portions may be flush with the first surface of the housing, and a second portion of each of the conductive housing portions may be flush with the second surface of the housing. The housing may have a first side and a second side, a first portion of each of the conductive housing portions may be exposed on the first side of the housing, and a second portion of each of the conductive housing portions may be exposed on the second side of the housing.

The housing may have a curved surface and a flat surface, a first portion of each of the conductive housing portions may be flush with the curved surface, and a second portion of each of the conductive housing portions may be flush with the flat surface of the housing. The curved surface may be disposed on a side portion of the housing, and the flat surface may be disposed on a top portion of the housing.

The conductive housing portions and the non-conductive housing portion may be formed so that no portion of any of the conductive housing portions comes into direct contact with the gas-sensing agent. The conductive housing portions may form a leakage detector, and the conductive housing portions may have a relatively high resistance between them in the absence of gas-sensing agent coming into contact with them and a relatively low resistance between them in the presence of gas-sensing agent coming into contact with them.

These and other features and advantages of the present invention will be apparent to those of ordinary skill in the art in view of the detailed description of the preferred embodiment, which is made with reference to the drawings, a brief description of which is provided below.

DETAILED DESCRIPTION OF A PREFERRED EMBODIMENT

Figure 1:
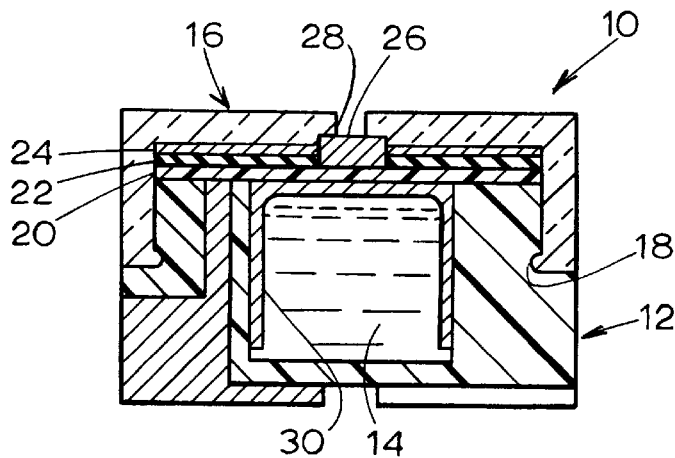
FIG. 1 is a cross-sectional view of a preferred embodiment of a gas sensor in accordance with the invention.

A preferred embodiment of an electrochemical sensor 10 in accordance with the invention is illustrated in FIG. 1. The sensor 10 has a housing composed of a first, generally cup-shaped housing portion 12 (see also FIG. 4) in which a receptacle 14 for the storage of an electrolyte or gas-sensing agent is formed and a second housing portion in form of a snap-fit cover 16 which is retained on the cup-shaped housing portion 12 via an annular rib 18, integrally formed with the cover 16, which rests in a matching annular groove formed in the housing portion 12.

A flat circular electrode support element, in the form of a sheet 20, a rubber gasket 22, and a leakage detector in the form of a leakage-indicating sheet 24 are disposed between the housing portion 12 and the cover 16. The rubber gasket 22 and the sheet 24 are flat and circular and each have a central hole formed therein in which a small cylindrical filter 26 is disposed. The leakage-indicating sheet 24 may be composed of a paper-like substrate, such as Paper No. BSF-65 commercially available from Whatman Specialty Co., impregnated with a conventional agent, such as dimethyl yellow, which changes color (in this case to red) when the gas-sensing agent comes into contact with it. The change in color can be viewed through the cover 16, which is formed of a transparent The cover 16 has an opening or sensing hole 28 formed therein directly above the filter 26 so as to expose the filter 26 to the ambient atmosphere to be sensed by the gas sensor 10. The purpose of the filter 26, which may be a rubber charcoal filter, is to prevent certain gases (which are not to be sensed) that may interfere with the sensing of the desired gas(es) from passing into the interior of the sensor 10 where the gas-sensing reaction takes place. The electrode support sheet 20 is hydrophobic to prevent the liquid gas-sensing agent from escaping from the sensor 10 via the sensing hole 28 but allows passage there through of the gaseous atmosphere to be sensed.

The gas sensor 10 includes a wick 30, which may be composed of glass paper, for example. The wick 30 includes a first portion, shown horizontally in FIG. 1, which abuts the underside of the electrode support sheet 20 and several portions which extend downwardly into the gas-sensing agent disposed in the receptacle 14. The purpose of the wick 30 is to maintain the underside of the electrode support sheet 20 (which has three electrodes formed thereon) in fluid contact with the gas-sensing agent. Where the gas sensor 10 is used to detect the presence of carbon monoxide, the gas-sensing agent may be a 30% sulfuric acid gel.

Figure 3:
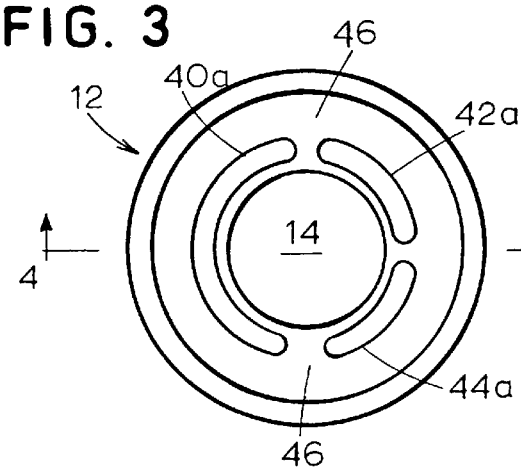
FIGS. 3–6 are various views of a housing portion of the sensor of FIG. 1 in which a receptacle for the storage of a gas-sensing agent is formed.
Figure 4:
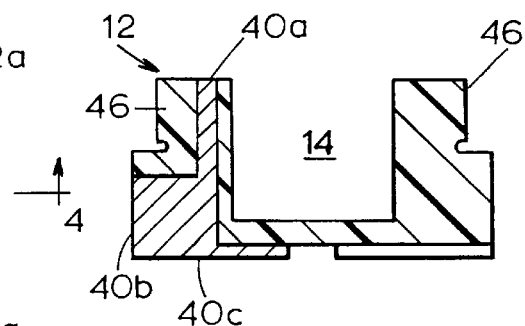
Figure 5:
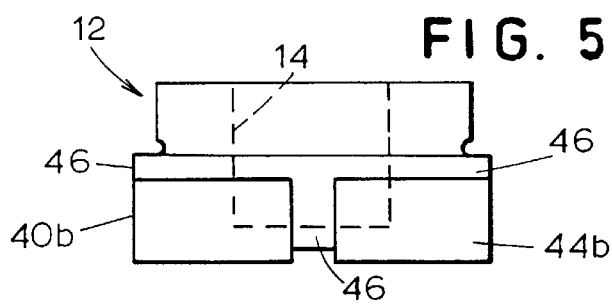
Figure 6:
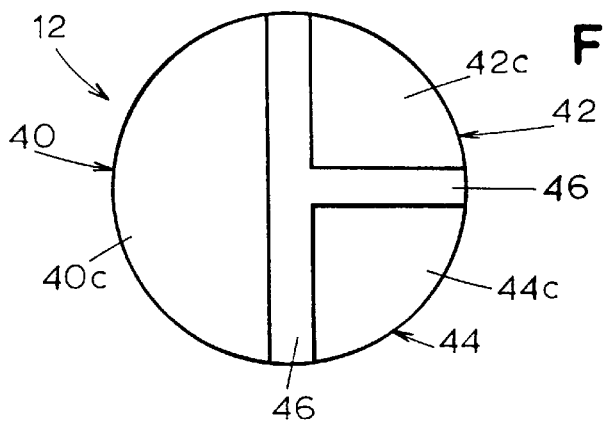

FIG. 3 is a top view of the cup-shaped housing portion 12 having the receptacle 14 formed therein. The cup-shaped housing 12 has three conductive housing portions 40, 42, 44, each of which serves as an electrical conductor. The three conductive portions 40, 42, 44 are electrically isolated from each other by the remaining non-conductive portions 46 of the housing 12. The conductive portion 40 is composed of three portions: an arcuate upper portion 40a having a relatively small radial width, a side portion 40b having a relatively large radial width, and a bottom portion 40c, all three of which are shown in FIG. 4. The side portion 40b acts as a side contact surface at which an electrical connection can be made, and the bottom portion 40c acts as a bottom contact surface at which an electrical connection can be made. The shapes of the conductive portions 42, 44 are similar to that of the conductive portion 40 in that they each have an arcuate upper portion (e.g. portion 44a) having a relatively small radial width, a side portion (e.g. portion 44b) having a relatively large radial width, and a bottom portion (e.g. portion 44c).

It is not necessary that the conductive housing portions 40, 42, 44 have both side and bottom portions; the provision of both side and bottom portions simply increases the area to which electrical connection may be made. The shape of the conductive portions 40, 42, 44 may be varied from those shown in FIGS. 3–6.

Figure 2:
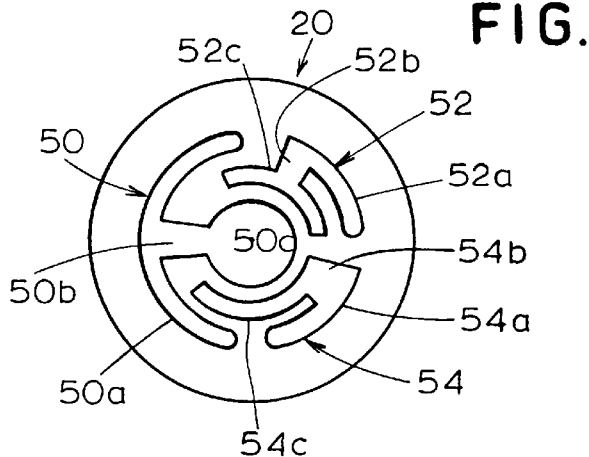
FIG. 2 is an illustration of an electrode support sheet used in the sensor of FIG. 1.

The electrode support sheet 20, the bottom surface of which is shown in FIG. 2, has three conductive electrode patterns 50, 52, 54 formed thereon. The pattern 50, which acts as a working electrode, includes a first central portion 50c, a second portion 50a, and a third portion 50b which electrically interconnects the portions 50a, 50c. The pattern 52, which acts as a reference electrode, and the pattern 54, which acts as a counter electrode, are similarly composed of three conductive portions 52a, 52b, 52c, 54a, 54b, 54c. The electrode patterns 50, 52, 54 may comprise platinum powder disposed on a substrate composed of TEFLON brand material in a conventional manner.

When the electrode support sheet 20 is placed on top of the housing portion 12, the conductive portions 50a, 52a, 54a of the electrode support sheet 20 are aligned and make contact with the arcuate conductive portions 40a, 42a, 44a of the housing 12. The electrode support sheet 20 may be provided with an alignment mechanism, such as a tab (not shown), to ensure that the conductive portions 50a, 52a, 54a are accurately aligned with the conductive portions 40a, 42a, 44a.

In the manufacture of the gas sensor 10, the cup-shaped housing 12 is formed via a conventional dual-injection molding process described as follows. First, the housing 12 without the three conductive portions 40, 42, 44 is injection-molded in a first mold with a non-conductive plastic, such as polypropylene. The result of the first mold will be a housing portion 12 as shown in FIGS. 3–6, but with air being present where the conductive portions 40, 42, 44 are shown. The housing portion 12 is then placed in a second mold, and the conductive portions 40, 42, 44 are injection-molded with a conductive plastic, such as polypropylene having carbon or other conductive fragments melted therein. The result of this conventional dual-molding process is the housing 12 shown in FIGS. 3–6 in which the non-conductive portions 46 and the conductive portions 40, 42, 44 together form a unitary construction.

Figure 7A:
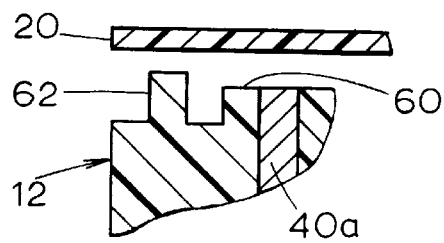
FIGS. 7A and 7B illustrate the formation of a heat seal utilized in the sensor of FIG. 1.
Figure 7B:
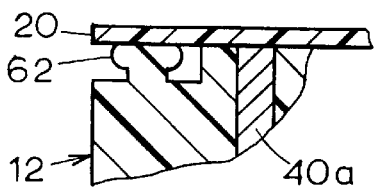

After the cup-shaped housing 12 is formed, a suitable gas-sensing agent is disposed within the receptacle 14, and then the wick 30 is disposed over the gas-sensing agent. The receptacle 14 is then sealed via a heat-sealing process to give it a liquid-tight seal. Referring to FIG. 7A, a portion of the sidewall of the cup-shaped housing 12 and a portion of the electrode support sheet 20 are shown enlarged. The cup-shaped housing 12 has an upper surface 60 and a meltable member 62 having an upper surface which is at a greater elevation than the surface 60. During the heat-sealing process, the electrode support sheet 20 is forced downwards over the top of the cup-shaped housing 12 by a flat heated platen (e.g. 210° C.) for a predetermined period of time (e.g. five seconds). As a result, the meltable member 62 will melt, as shown in FIG. 7B, to form a heat-sealed bond with the electrode support sheet 20. It should be understood that since the overall shape of the meltable member 62 is circular and since the circular member 62 surrounds the entire outer periphery of the cup-shaped housing 12, a heat-sealed bond is formed about the entire periphery of the housing 12 so that the gas-sensing agent is completely confined within the receptacle 14.

To facilitate ease of manufacture, the gas-sensing agent may be introduced into the housing 12, after the heat seal is formed as described above, through a hole or tube in the bottom of the housing 12 (with the housing 12 being inverted). After the gas-sensing agent is added, the hole or tube is permanently closed (e.g. in the case of a meltable tube, by melting the tube closed).

One advantage of the manner of making the heat seal described above is that the TEFLON brand material of the electrode support element 20 is bonded directly to the polypropylene plastic of the cup-shaped housing 12, with no conductive portions 40, 42, 44 or 50, 52, 54 coming into contact with the seal. That is advantageous because the heat-sealing of TEFLON brand material and polypropylene forms a relatively strong bond, while the presence of conductive portions, such as those formed by platinum powder, may result in a weaker bond.

After the heat-sealed bond is formed, the rubber gasket 22, the leakage-indicating sheet 24, and the filter 26 are placed on the electrode support sheet 20, and the cover 16 is snap-fit over the assembly and is retained in place by the annular rib 18. The vertical location of the rib 18 with respect to the underside of the cover 16 is dimensioned so that, when the cover 16 snap-fit onto the housing portion 12, the underside of the cover 16 exerts a pressure of at least about 20 psi, and preferably about 25 psi, on the electrode support sheet 20, thus ensuring that the conductive portions 50a, 52a, 54a of the electrode support sheet 20 are always in electrical contact with the conductive portions 40a, 42a, 44a of the housing 12.

In operation, to detect a gas, a constant voltage is placed between the working electrode 50c and the reference electrode 52c via the conductive contact portions 40c and 42c (which are electrically connected to the electrodes 50c, 52c, respectively). Then, upon the presence of the gas being detected through the sensing hole 28, an electrical current will be induced between the working electrode 50c and the counter electrode 54c, which current can be detected and measured by a conventional current sensing circuit attached to the conductive contact portions 40c and 44c (which are electrically connected to the electrodes 50c and 54c).

Figure 8:
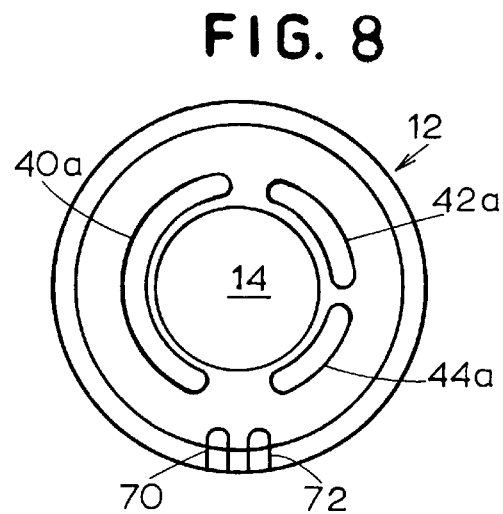
FIGS. 8 and 9 illustrate an alternative embodiment of a gas sensor in accordance with the invention.
Figure 9:
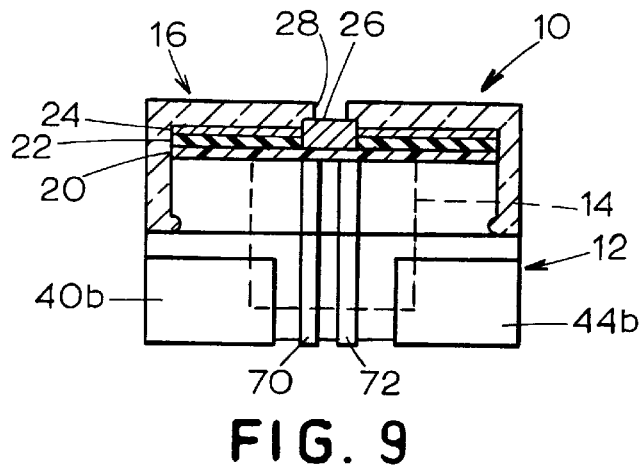

A second embodiment of the gas sensor 10 is illustrated in FIGS. 8 and 9. Referring to those figures, the cup-shaped housing 12 is modified by the addition of two conductive housing portions 70, 72 which together act as a second type of leakage detector. In the event that any gas-sensing agent leaks from the receptacle 14 and bridges the gap between the two conductive housing portions 70, 72, the electrical resistance between those two portions 70, 72 will change from a relatively large value (due to the non-conductive housing portion separating the portions 70, 72) to a relatively small value (since the gas-sensing agent has a relatively low electrical resistance). This significant change in resistance can be detected in a conventional manner by a conventional detecting circuit connected to both of the conductive portions 70, 72. The conductive portions 70, 72 are formed in the same manner as the conductive portions 40, 42, 44 formed during the dual-injection molding process described above.

Additional modifications and alternative embodiments of the invention will be apparent to those skilled in the art in view of the foregoing description. This description is to be construed as illustrative only, and is for the purpose of teaching those skilled in the art the best mode of carrying out the invention. The details of the structure and method may be varied substantially without departing from the spirit of the invention, and the exclusive use of all modifications which come within the scope of the appended claims is reserved.

What is claimed is:

1. A gas sensor assembly comprising:
   a housing having a receptacle formed therein;
   a gas-sensing agent disposed in said receptacle; and
   a plurality of electrodes disposed in fluid contact with said gas-sensing agent,
   said housing having a non-conductive housing portion with a plurality of spaces formed therein and a plurality of conductive housing portions disposed within said spaces of said non-conductive housing portion,
      each of said conductive housing portions being conductively separated from each other by said non-conductive housing portion,
      each of said conductive housing portions being conductively separated from said electrodes, and
      each of said conductive housing portions being composed of a conductive plastic material.

2. A gas sensor as recited in claim 1 wherein said housing has a contact surface that is formed by a portion of said non-conductive housing portion and a portion of each of said conductive housing portions, wherein said gas sensor assembly additionally comprises an electrode plate disposed adjacent said contact surface of said housing, and wherein said electrodes are disposed on said electrode plate.

3. A gas sensor as recited in claim 1 wherein said housing has a surface and wherein said surface of said housing is formed by a portion of said non-conductive housing portion and a portion of each of said conductive housing portions.

4. A gas sensor as recited in claim 1 wherein said conductive housing portions and said non-conductive housing portion are formed so that no portion of any of said conductive housing portions comes into direct contact with said gas-sensing agent.

5. A gas sensor as recited in claim 1 wherein said housing has a first surface and a second surface and wherein a first portion of one of said conductive housing portions is flush with said first surface of said housing and wherein a second portion of said one conductive housing portion is flush with said second surface of said housing.

6. A gas sensor as recited in claim 1 wherein said housing has a first surface and a second surface and wherein a first portion of each of said conductive housing portions is flush with said first surface of said housing and wherein a second portion of each of said conductive housing portions is flush with said second surface of said housing.

7. A gas sensor as recited in claim 1 wherein said housing has a first side and a second side and wherein a first portion of each of said conductive housing portions is exposed on said first side of said housing and wherein a second portion of each of said conductive housing portions is exposed on said second side of said housing.

8. A gas sensor as recited in claim 1 wherein said housing has a first side and a second side and wherein a first portion of one of said conductive housing portions is exposed on said first side of said housing and wherein a second portion of said one conductive housing portion is exposed on said second side of said housing.

9. A gas sensor as recited in claim 1 wherein said housing has a curved surface and a flat surface and wherein a first portion of each of said conductive housing portions is flush with said curved surface of said housing and wherein a second portion of each of said conductive housing portions is flush with said flat surface of said housing.

10. A gas sensor as recited in claim 9 wherein said curved surface is disposed on a side portion of said housing and wherein said flat surface is disposed on a top portion of said housing.

11. A gas sensor as recited in claim 1 wherein conductive housing portions form a leakage detector and wherein said conductive housing portions have a relatively high resistance between them in the absence of gas-sensing agent coming into contact with them and a relatively low resistance between them in the presence of gas-sensing agent coming into contact with them.

12. A gas sensor assembly comprising:

a housing having a receptacle formed therein;

a gas-sensing agent disposed in said receptacle; and a plurality of electrodes disposed in fluid contact with said gas-sensing agent, said housing having a non-conductive housing portion and a plurality of conductive housing portions, each of said conductive housing portions being conductively separated from each other by said non-conductive housing portion, each of said conductive housing portions being conductively separated from said electrodes, and each of said conductive housing portions being composed of a conductive plastic material.

13. A gas sensor as recited in claim 12 wherein said housing has a contact surface that is formed by a portion of said non-conductive housing portion and a portion of each of said conductive housing portions, wherein said gas sensor assembly additionally comprises an electrode plate disposed adjacent said contact surface of said housing, and wherein said electrodes are disposed on said electrode plate.

14. A gas sensor as recited in claim 12 wherein said housing has a surface and wherein said surface of said housing is formed by a portion of said non-conductive housing portion and a portion of each of said conductive housing portions.

15. A gas sensor as recited in claim 12 wherein said housing has a first surface and a second surface and wherein a first portion of one of said conductive housing portions is flush with said first surface of said housing and wherein a second portion of said one conductive housing portion is flush with said second surface of said housing.

16. A gas sensor as recited in claim 12 wherein said housing has a first surface and a second surface and wherein a first portion of each of said conductive housing portions is flush with said first surface of said housing and wherein a second portion of each of said conductive housing portions is flush with said second surface of said housing.

17. A gas sensor as recited in claim 12 wherein said housing has a first side and a second side and wherein a first portion of each of said conductive housing portions is exposed on said first side of said housing and wherein a second portion of each of said conductive housing portions is exposed on said second side of said housing.

18. A gas sensor as recited in claim 12 wherein said housing has a first side and a second side and wherein a first portion of one of said conductive housing portions is exposed on said first side of said housing and wherein a second portion of said one conductive housing portion is exposed on said second side of said housing.

19. A gas sensor as recited in claim 12 wherein said housing has a curved surface and a flat surface and wherein a first portion of each of said conductive housing portions is flush with said curved surface of said housing and wherein a second portion of each of said conductive housing portions is flush with said flat surface of said housing.

20. A gas sensor as recited in claim 19 wherein said curved surface is disposed on a side portion of said housing and wherein said flat surface is disposed on a top portion of said housing.

* * * * *